US012648715B2

(12) United States Patent
Pretzer-Aboff et al.

(10) Patent No.: US 12,648,715 B2
(45) Date of Patent: Jun. 9, 2026

(54) VIBRATIONAL DEVICE AND METHODS FOR MITIGATING SYMPTOMS OF FREEZING OF GAIT

(71) Applicants: Ingrid Pretzer-Aboff, Newark, DE (US); Richard D. Martin, Newark, DE (US); David Bruce Chase, Newark, DE (US); Scott Jones, Newark, DE (US); John F. Rabolt, Greenville, DE (US)

(72) Inventors: Ingrid Pretzer-Aboff, Newark, DE (US); Richard D. Martin, Newark, DE (US); David Bruce Chase, Newark, DE (US); Scott Jones, Newark, DE (US); John F. Rabolt, Greenville, DE (US)

(73) Assignee: University of Delaware, Newark, DE (US)

( * ) Notice: Subject to any disclaimer, the term of this patent is extended or adjusted under 35 U.S.C. 154(b) by 565 days.

(21) Appl. No.: 17/413,337

(22) PCT Filed: Dec. 12, 2019

(86) PCT No.: PCT/US2019/065952
§ 371 (c)(1),
(2) Date: Jun. 11, 2021

(87) PCT Pub. No.: WO2020/123789
PCT Pub. Date: Jun. 18, 2020

(65) Prior Publication Data
US 2022/0015500 A1 Jan. 20, 2022

Related U.S. Application Data

(60) Provisional application No. 62/778,489, filed on Dec. 12, 2018.

(51) Int. Cl.
*A61B 5/11* (2006.01)
*A43B 3/34* (2022.01)
(Continued)

(52) U.S. Cl.
CPC ................ *A61B 5/112* (2013.01); *A43B 3/34* (2022.01); *A43B 7/147* (2013.01); *A61H 3/00* (2013.01);
(Continued)

(58) Field of Classification Search
CPC .. A43B 7/147; A43B 3/34; A43B 7/00; G16H 20/30; A61H 23/02;
(Continued)

(56) References Cited

U.S. PATENT DOCUMENTS 8,692,675 B2 4/2014 Agrawal et al.
9,311,827 B1 * 4/2016 Alqahtani ............ G09B 21/007
(Continued)

FOREIGN PATENT DOCUMENTS

EP 2444104 A2 4/2012
GB 2539264 A * 12/2016 ......... A61H 23/0254
(Continued)

OTHER PUBLICATIONS

International Preliminary Report on Patentability for International Application No. PCT/US2019/065952, dated Jun. 8, 2021, 10 pages.
(Continued)

*Primary Examiner* — Bradley H Philips
*Assistant Examiner* — Tyler A Raubenstraw
(74) *Attorney, Agent, or Firm* — Buchanan Ingersoll & Rooney PC

(57) ABSTRACT
A device adapted to be secured to the foot of a user includes one or more vibration actuators configured to provide vibrations to the user's foot, one or more force or acceleration sensors configured to sense forces or acceleration exerted by the user's foot, and a controller configured to operate the vibration actuators in a continuous mode to provide intermittent vibration to the user's foot independent of informa-
(Continued)

tion sensed by the force or acceleration sensors. The vibration includes a first period of continuous vibration followed by a second period of no vibration followed by a third period of continuous vibration. The device may also be configured to operate in a feedback mode.

19 Claims, 6 Drawing Sheets

(51) Int. Cl.

| | |
|---|---|
| *A43B 7/1455* | (2022.01) |
| *A61H 3/00* | (2006.01) |
| *A61H 23/02* | (2006.01) |
| *G16H 20/30* | (2018.01) |

(52) U.S. Cl.
CPC ............. *A61H 23/02* (2013.01); *G16H 20/30* (2018.01); *A61H 2201/1642* (2013.01); *A61H 2201/165* (2013.01); *A61H 2201/5061* (2013.01); *A61H 2201/5084* (2013.01); *A61H 2201/5097* (2013.01); *A61H 2205/12* (2013.01)

(58) Field of Classification Search
CPC ...... A61H 2201/1642; A61H 2201/165; A61H 2201/5061; A61H 2201/5084; A61H 2201/5097; A61H 2205/12; A61H 3/00; A61H 1/0266; A61B 5/1101; A61B 5/1038; A61B 5/112; A61B 5/11
See application file for complete search history.

(56) References Cited

U.S. PATENT DOCUMENTS

| | | | | |
|---|---|---|---|---|
| 9,452,287 | B2 * | 9/2016 | Rosenbluth | ........ A61N 1/36178 |
| 9,591,993 | B2 * | 3/2017 | Morris Bamberg | . A61B 5/6807 |
| 9,707,462 | B2 * | 7/2017 | Reynolds, III | ....... A61B 5/1121 |
| 9,782,122 | B1 * | 10/2017 | Pulliam | ................ A61B 5/4839 |
| 10,034,622 | B1 * | 7/2018 | Mahmoud | ................ A43B 3/34 |
| 10,076,460 | B2 * | 9/2018 | Harry | ................... A61H 39/002 |
| 10,595,749 | B1 * | 3/2020 | Javitt | ................... A61B 5/7455 |
| 10,921,886 | B2 * | 2/2021 | Connor | .................. A61B 5/389 |
| 2007/0203435 | A1 * | 8/2007 | Novak | ................... A43B 17/00 |
| | | | | 601/46 |
| 2008/0082025 | A1 * | 4/2008 | Hughes | ................ A61B 5/6829 |
| | | | | 600/595 |
| 2009/0240171 | A1 * | 9/2009 | Morris Bamberg | . A61B 5/0002 |
| | | | | 600/595 |
| 2011/0251520 | A1 * | 10/2011 | Shieh | ........................ A43D 1/02 |
| | | | | 600/587 |
| 2012/0184878 | A1 * | 7/2012 | Najafi | ................... A61B 5/4833 |
| | | | | 600/592 |
| 2013/0192071 | A1 * | 8/2013 | Esposito | ................ A43B 17/00 |
| | | | | 324/693 |
| 2014/0121574 | A1 * | 5/2014 | Chladek | ............. A61N 1/36003 |
| | | | | 601/27 |

| | | | | |
|---|---|---|---|---|
| 2015/0257679 | A1 * | 9/2015 | Ross | ....................... G01L 5/162 |
| | | | | 702/44 |
| 2016/0058326 | A1 * | 3/2016 | Winfree | ................. A61B 5/112 |
| | | | | 600/592 |
| 2016/0284231 | A1 * | 9/2016 | Walsh | ................ G09B 19/0038 |
| 2016/0324445 | A1 * | 11/2016 | Kim | ...................... A61B 5/6802 |
| 2017/0011210 | A1 * | 1/2017 | Cheong | ................... A61B 5/681 |
| 2017/0087416 | A1 * | 3/2017 | Hu | .......................... G16H 20/30 |
| 2017/0112712 | A1 * | 4/2017 | Chawan | ............ A61H 23/0245 |
| 2017/0188950 | A1 * | 7/2017 | Gazdag | ................ A61B 5/1038 |
| 2017/0273851 | A1 * | 9/2017 | Larmer | ................... A61F 13/08 |
| 2018/0132758 | A1 * | 5/2018 | Benford | ................. A61B 5/112 |
| 2018/0168917 | A1 * | 6/2018 | Bushara | .............. A61H 9/0085 |
| 2018/0206775 | A1 * | 7/2018 | Saria | .................... A61B 5/6898 |
| 2018/0264263 | A1 * | 9/2018 | Rosenbluth | ........ A61N 1/36031 |
| 2018/0333078 | A1 * | 11/2018 | Malawey | ................. A43B 3/34 |
| 2019/0175106 | A1 * | 6/2019 | Langer | .................. G16H 50/30 |
| 2019/0298605 | A1 * | 10/2019 | Rabolt | .............. A61H 23/0263 |
| 2021/0022666 | A1 * | 1/2021 | Malawey | ............. A43B 17/006 |

FOREIGN PATENT DOCUMENTS

| | | | | | |
|---|---|---|---|---|---|
| WO | WO-2015088863 | A2 * | 6/2015 | ............ | A61B 5/112 |
| WO | WO-2015187712 | A1 * | 12/2015 | ........... | A61B 5/1101 |
| WO | WO-2016166281 | A1 * | 10/2016 | ........... | A61B 5/1116 |
| WO | WO-2019086997 | A2 * | 5/2019 | ............ | A61B 5/486 |
| WO | WO-2019134033 | A2 * | 7/2019 | ............ | A41B 11/00 |

OTHER PUBLICATIONS

International Search Report and Written Opinion for International Application No. PCT/US2019/065952, dated Feb. 21, 2020, 10 pages.

Abruzzese et al., "Sensorimotor Integration in movement disorders", Mov. Disord., Mar. 18, 2003, (3):231-240.

Ariizumi et al., "Effects of Whole Body Vibration on Biogenic Amines in Rat Brain", British Journal of Industrial Medicine, vol. 42, No. 2, Feb. 1985, pp. 133-136.

Hallet et al., "The Intrinsic and Extrinsic Aspects of Freezing of Gait", Mov. Disord., 2008 ; 23(0 2): S439-S443.

MacKay-Lyons, M., "Central Pattern Generation of Locomotion: A Review of the Evidence", Physical Therapy, vol. 82, No. 1, Jan. 2002, pp. 69-83.

Nakamura et al., "Activation of Cerebral Dopaminergic Systems by Noise and Whole-Body Vibration", Environmental Research, 1992, 57, pp. 10-18.

Post et al., "Intermittent Versus Continuous Stimulation: Effect of Time Interval on the Development of Sensitization or Tolerance", Life Sciences, vol. 26, pp. 1275-1282.

Winfree et al., "The Effect of Step-Synchronized Vibration on Patients With Parkinson's Disease: Case Studies on Subjects With Freezing of Gait or an Implanted Deep Brain Stimulator", IEEE transactions on Neural Systems and Rehabilitation Engineering: a publication of the IEEE Engineering in Medicine and Biology Society, Mar. 2013, 7 pages.

Winfree, et al., "Identifying when Changes to Parkinsonian Gait Occur within a Vibratory Intervention Study", Journal of Parkinson's Disease, 2013, vol. 3, (suppl. 1), 1 page. Abstract only.

* cited by examiner

100

130c

130b

130a

150a

150b

170

190

110

300

310

320

Enable user to ambulate

Provide vibratory feedback to user's foot based on forces sensed during ambulation

350

VIBRATIONAL DEVICE AND METHODS FOR MITIGATING SYMPTOMS OF FREEZING OF GAIT

CROSS REFERENCE TO RELATED APPLICATIONS

This application is a U.S. national phase application of International Application No. PCT/US2019/065952, filed Dec. 12, 2019 claiming priority to U.S. Patent Application No. 62/778,489, titled "Improvements on PD Shoe," filed on Dec. 12, 2018, the contents of which is incorporated herein by reference in their entirety.

STATEMENT REGARDING FEDERALLY SPONSORED RESEARCH

This invention was made with United States government support under EPSCoR Grant No. 1301765, awarded by the National Science Federation. The U.S. government has certain rights in the invention.

BACKGROUND OF THE INVENTION

U.S. Pat. No. 8,692,675 B2, titled VIBRATORY FEED-BACK SYSTEMS AND METHODS, owned by the common Assignee of this invention and incorporated herein by reference in its entirety, describes a vibratory feedback system in the nature of a footwear adapted to be secured to a foot of a user and a methods for improving the gait of a user based upon feedback signals generated during ambulation by patients. U.S. Published Patent Application Ser. No. US20160058326A1, titled GAIT AND MOBILITY ASSESSMENT SYSTEMS AND METHODS, owned by the common Assignee of this invention, also incorporated herein by reference in its entirety, describes footwear adapted to be secured to a foot of a user and methods for assessing the gait of a user based upon information generated by an assessment system.

Experiments conducted using embodiments of the subject systems have led to improvements and new methods of using specialized footwear with sensors and vibration actuators, as further described herein.

SUMMARY OF THE INVENTION

One aspect of the invention comprises a vibratory system including a device adapted to be secured to a foot of a user, and one or more vibration actuators mounted on the device, the one or more vibration actuators configured to provide vibrations to the foot of the user, and one or more force or acceleration sensors mounted on the device, the one or more force or acceleration sensors configured to sense forces or acceleration exerted by the foot of the user. A controller connected to the one or more vibration actuators is config-ured to operate the one or more vibration actuators in a continuous mode in which the one or more vibration actua-tors are continuously activated for a first duration to provide a vibration to the foot of the user that is not dependent upon information sensed by the one or more force or acceleration sensors. The controller is configured to provide the continu-ously activated vibration intermittently by providing sequentially a first period of continuous vibration, a second period of no vibration, and a third period of continuous vibration.

The controller may be connected to a data storage com-ponent configured to store data generated by the one or more force or acceleration sensors. The controller may be pro-grammed to transmit the data received from the plurality of force or acceleration sensors to a remote monitoring unit via a wireless communication device in communication with the controller and with the remote monitoring unit. The con-troller may be programmed to receive instructions for oper-ating the system from the remote monitoring unit via the wireless communication device. The controller may further be programmed to operate in a feedback mode in which the plurality of vibration actuators are activated to provide vibration to the foot of the user based directly upon infor-mation sensed by the one or more force or acceleration sensors. The controller may programmed to process infor-mation sensed by the one or more force or acceleration sensors to determine an activity of the wearer, and to impose a continuous mode of vibration selected based upon the activity so determined.

The one or more vibration actuators may include at least one vibration actuator disposed on the device in a position configured to transmit vibration to a $3^{rd}$ toe of the wearer's foot. The one or more vibration actuators may further include at least one vibration actuator disposed on the device in a position configured to transmit vibration to at least one of a $2^{nd}$ toe or a $4^{th}$ toe of the wearer's foot. The one or more vibration actuators may still further include at least one vibration actuator disposed on the device in a position configured to transmit vibration to a medial aspect of the ankle.

Another aspect of the invention is a method of improving the gait of a user. The method comprises securing a vibratory system to a foot of the user and operating the system in a continuous mode. The vibratory system comprises a device adapted to be secured to a foot of a user, a controller coupled to one or more vibration actuators mounted on the device and configured to provide vibrations to the foot of the user and one or more force or acceleration sensors mounted on the device and configured to sense forces or acceleration exerted by the foot of the user. The continuous mode comprises the sequential steps of providing vibration to the foot of the user for a first duration of time that is not dependent upon information sensed by the one or more force or acceleration sensors, then providing no vibration to the foot of the user for a second duration of time that is not dependent upon information sensed by the one or more force or acceleration sensors, and then providing vibration to the foot of the user for a third duration that is not dependent upon information sensed by the one or more force or acceleration sensors. The method may comprise a treatment for Parkinson's Disease and may comprise subjecting the wearer to a vibration treatment protocol comprising multiple cycles of the foregoing steps per day for multiple days. In particular, the treatment protocol may comprise two con-secutive days of treatment, followed by a day of no treat-ment, followed by two consecutive days of treatment.

The method may further comprise the step of operating the system in feedback mode for a fourth duration of time before or after the first or third durations in which the one or more vibration actuators are repeatedly activated and deac-tivated to provide vibration or no vibration to the foot of the user based upon information sensed by the one or more force or acceleration sensors. The method may further comprise the steps of monitoring the forces sensed by the one or more force or acceleration sensors during ambulation by the user, and one or more of storing the data received from the one or more force or acceleration sensors for later analysis and transmitting the data generated by the one or more force or acceleration sensors to a remote monitoring unit.

The method may further comprise receiving in the controller instructions from the remote monitoring unit for operating the system. The method may comprise providing vibration to a $3^{rd}$ toe of the wearer's foot, providing vibration to at least one of a $2^{nd}$ toe or a $4^{th}$ toe of the wearer's foot, and/or providing vibration to transmit vibration to a medial aspect of the ankle.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. This emphasizes that according to common practice, the various features of the drawings are not drawn to scale unless otherwise indicated. On the contrary, the dimensions of the various features may be expanded or reduced for clarity. Included in the drawings are the following figures.

DETAILED DESCRIPTION OF THE INVENTION

The systems and methods disclosed herein are usable to improve a user's gait, e.g., by developing or maintaining the user's natural walking ability. Generally, these systems and related methods for generating vibration that assists a user walking under the user's own power to avoid Freezing of Gait (FoG). The systems and methods disclosed herein are particularly suitable for users with degenerative neurological disorders, such as but not limited to, Parkinson's disease (PD).

Figure 1A:
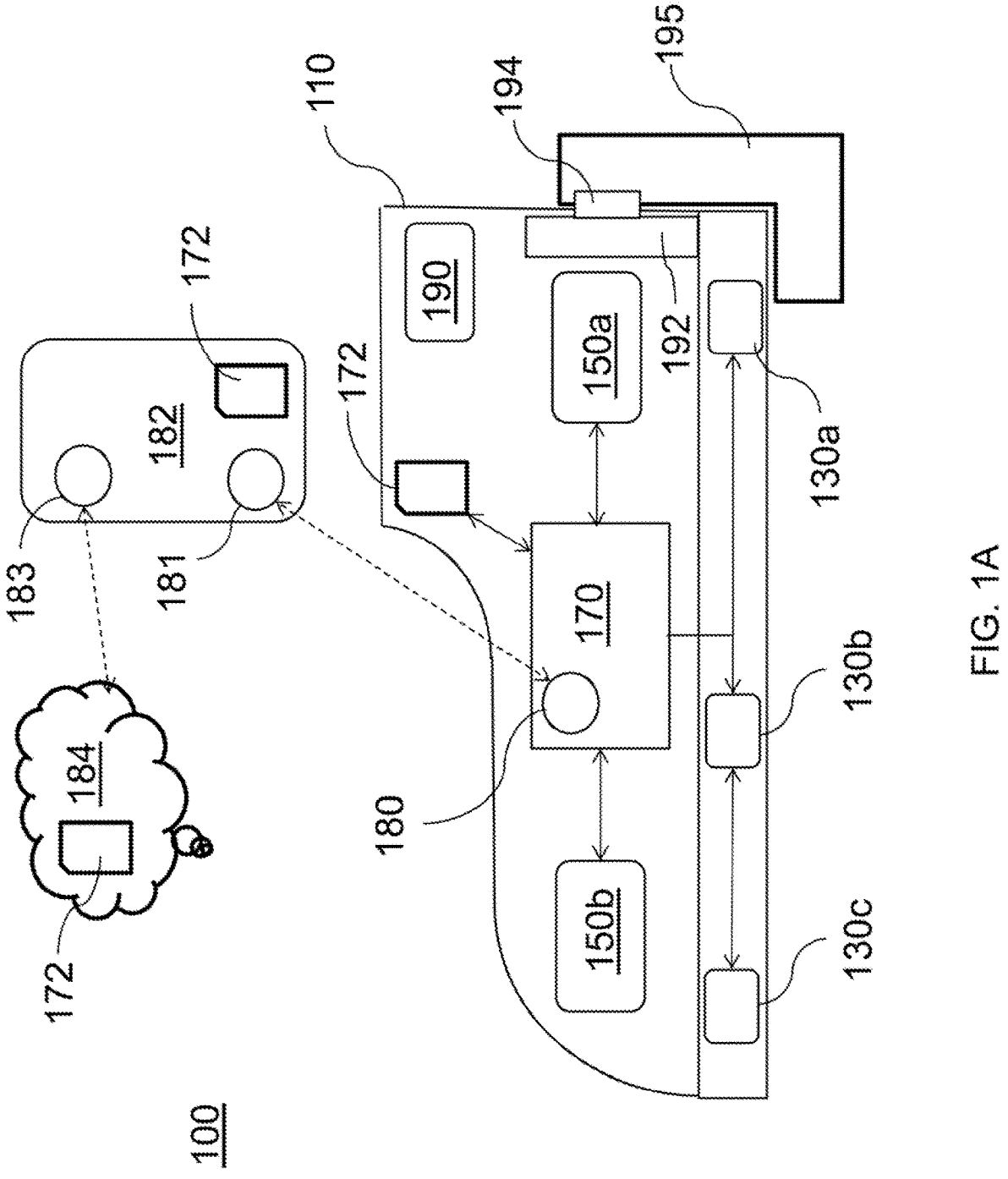
FIG. 1A is a schematic diagram illustrating an exemplary vibratory feedback system in accordance with aspects of the present invention.
Figures 1B, 1C:
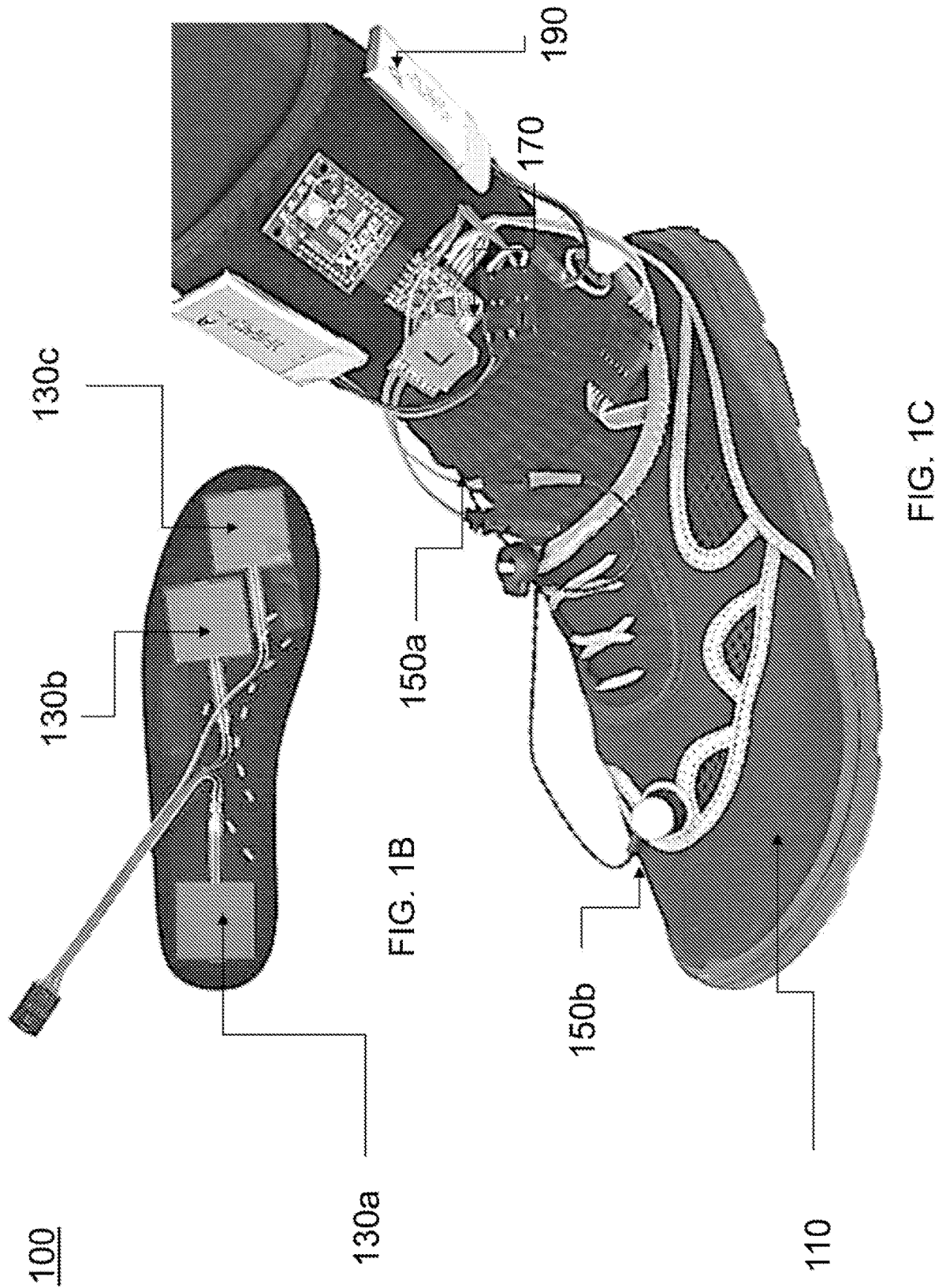
FIGS. 1B and 1C are images of the vibratory feedback system of FIG. 1A.

Referring now to the drawings, FIGS. 1A-1C illustrate an exemplary vibratory system 100 in accordance with aspects of the invention. Vibratory system 100 is usable to improve the gait of a user. As a general overview, vibratory system 100 includes a shoe 110, one or more force or acceleration sensors 130a-130c, 190, one or more vibration actuators 150a and 150b, and a controller, such as a microprocessor 170. Additional details of vibratory feedback system 100 are described herein.

As originally described in U.S. Pat. No. 8,692,675, device 110 is adapted to be secured to the foot of the user of vibratory system 100. As used herein and in the application to which the present application claims priority, the term "shoe" is not intended to refer to any particular category or style of footwear, and the term PD Shoe is not intended to refer to systems and methods useful only in connection with Parkinson's Disease. The term "shoe" is intended to encompass any and all structures adapted to be secured to a user's foot, including what might be more commonly perceived to be a "sock," a "slipper," or a "stocking." Device 110 may desirably comprise flexible or elastic material, in order to enable use of device 110 by users having different sized feet. Device 110 may desirably be comprised of thin, non-cushioned material in order to improve conduction of vibrations to the user's foot. In an exemplary embodiment, device 110 comprises footwear similar in nature to what ordinary consumers may commonly refer to as a "water shoe." Other suitable structures for use as device 110 will be known to one of ordinary skill in the art from the description herein.

In the embodiment disclosed in U.S. Pat. No. 8,692,675, force sensors 130a-130c are mounted on device 110 in positions to enable them to sense forces exerted by the user's foot during standing or ambulation by the user, such as underneath the user's foot when device 110 is secured to the user's foot, e.g., in the sole of shoe 110. Accelerometer 190 is mounted on a position of device 110 in which it can sense movement of device 110. In the exemplary embodiment shown in FIG. 1A, force (e.g. pressure) sensors 130a-130c include a heel sensor 130a configured to sense a force exerted by the user's heel, a ball sensor 130b configured to sense a force exerted by the ball of the user's foot, and a toe sensor 130c configured to sense a force exerted by one or more of the user's toes. In an exemplary embodiment, microprocessor 170 is coupled to receive data from force sensors 130a-130c and/or accelerometer 190 representing the sensed movement. In a feedback mode of operation, the microprocessor may actuate vibration actuators 150a and 150b to provide a characteristic vibration to the user's foot, based on the movement of shoe 110 sensed by force sensors 130a-130c and/or accelerometer 190. In a continuous mode of operation, force sensors 130a-130c and/or accelerometer 190 may simply generate data to be used for later analysis, as described herein further.

Vibration actuators 150a and 150b are mounted in device 110 in a configuration that enables them to provide vibrations perceptible by the user's foot. Vibration actuators 150a and 150b may be spaced from each other to enable vibrations to be provided to different portions of the user's foot. U.S. Pat. No. 8,692,675 describes rear vibration actuator 150a mounted in a rear region of shoe 110, and front actuator 150b mounted in a front region of device 110, but discloses that the vibratory system 100 may include any number of one or more vibration actuators. Each of the vibration actuators 150a and 150b may be configured to provide a particular vibration having a controllable amplitude and frequency, including an independently controllable amplitude and frequency of vibration relative to other vibration actuators, such that the amplitude and/or frequency of vibration of vibration actuator 150a may be different than that of vibration actuator 150b.

As noted in U.S. Pat. No. 8,692,675, the frequency of vibrations provided by vibration actuators 150a,b may be selected to be in a range of frequencies most easily or effectively detected by the wearer. The invention is not limited to a particular frequency.

Controller 170, such as a microprocessor, controls the operation of vibratory system 100. Controller 170 is affixed to shoe 110, and is electrically coupled to force or acceleration sensors 130a-130c, 190 and vibration actuators 150a and 150b. In a feedback mode of operation (as described and claimed in U.S. Pat. No. 8,692,675), controller 170 receives data from force or acceleration sensors 130a-130c, 190 and is programmed to actuate vibration actuators 150*a* and 150*b* to provide a characteristic vibration to the user's foot, based on the forces sensed by force sensors 130*a*-130*c*. In a continuous vibration mode of operation, as described herein in more detail, actuation of the vibration actuators is not based upon feedback provided by the sensors, but rather provided continuously. The microprocessor may still receive and log data provided by the sensors, such as for later analysis of the user's gait while wearing the device. The microprocessor may also have time functionality, such as a clock and calendar synchronized to a known standard, for logging information coupled to the date and time the information was generated.

Vibratory system 100 may include a data storage component (not shown) for use in controlling vibratory feedback system 100, or storing data obtained during operation of vibratory system 100. In an exemplary embodiment, controller 170 may be configured to store data received from force sensors 130*a,b* (or any other sensors as described herein) in a data storage component 172, e.g. digital computer memory, such as an SD Card, to facilitate later analysis.

Vibratory system 100 may also include a wireless communication module 180, as shown in FIG. 1A operable to enable bi-directional communications (e.g. near-field wireless communications such as using Bluetooth® technology) between controller 170 and a corresponding wireless communication module 181 in remote monitoring unit 182 (e.g. a smart phone or other mobile computing device) and/or a device worn on the user's other foot. In an exemplary embodiment, controller 170 is programmed to transmit the data to the remote monitoring unit via wireless communication device 180. Controller 170 may further be programmed to receive data for actuating vibration actuators 150*a* and 150*b* from the remote monitoring unit via wireless communication device 180. Thus, the data component for storing information relating to the user's gait may be integral to the wearable device 100, the mobile computing device 182, or located "in the cloud" in server storage 184 that is remotely accessible via communications network (such as the Internet), such as transmitted by the mobile device via wireless communication module 183 to the server via WI-FI® equipment, cellular communications, and/or any communication protocol known in the art. Data may be communicated for storage in real time, or in bursts, depending upon connectivity of the mobile device and local storage capabilities. A centralized monitoring center may remotely monitor user data from multiple systems at the same time. Sensor data may be further processed and analyzed to identify characteristics of the user's gait, including as discussed in detail in U.S. Published Patent Application Ser. No. US20160058326A1.

The wireless communications modules 180, 181, 183 described herein may be selected based on the desired type and range of communication to be achieved by each. In embodiments in which modules 180 and 181 are configured to communicate locally (e.g. between a user of device 100 and a smart phone 182 in close proximity to the wearer, such as in a pocket of clothing also worn by the user), the modules may optimally comprise a near-field communications transceivers. In embodiments in which the communications module 183 in remote monitoring unit is configured to transmit the data over a larger distance (e.g. to be received by a remote server in the cloud 184), module 183 may comprise a radio-frequency of a cell-phone transceiver. Suitable transceivers for use as any of these communications modules are known to one of ordinary skill in the art from the description herein. The communications modules 180, 181, 183 are preferably transceivers capable of sending and receiving signals, even if their primary function is only sending or receiving, to permit sending acknowledgements of transmissions received, and receiving acknowledgements of transmissions sent.

Some embodiments may also include an altitude sensor (not shown) configured to sense a relative height of shoe and coupled to the controller. System 100 may also include a global positioning system (GPS) sensor not shown), such as integrated into the remote monitoring unit or mounted on the footwear device. Information provided by the GPS sensor regarding relative position of the device may be used for determining the type of environment (e.g., home, work, etc.) in which the user is located during the recordation of other information by the other sensors, and for selectively activating continuous and/or feedback operation based upon device location.

The system may also include a non-vibratory feedback component (not shown), such as a component configured to provide audio feedback (such as a speaker) or video feedback (such as a display screen) to the user, such as based on the user's ambulation in a feedback mode of operation, as further described in U.S. Published Patent Application Ser. No. US20160058326A1.

Vibratory system 100 is not limited to the above components, but may include alternative, additional, or fewer components, as would be understood by one of ordinary skill in the art.

Embodiments may include a charging cradle 190 for charging a power supply 192 embedded in the system and having a charging connection 194. The power supply is in electrical communication with the powered components of the device (electrical connections not shown, to reduce clutter).

Feedback Mode

U.S. Pat. No. 8,692,675 describes the operation of vibratory system 100 in a feedback mode, which description follows. In feedback operation, a user secures vibratory feedback system 100 to his or her foot, and ambulates under his or her own power. During ambulation, the user's foot naturally exerts a force on the surface being walked upon. Force sensors 130*a*-130*c* sense the force exerted by the user's foot and/or accelerometer 190 senses accelerations of the device attached to the user's foot, and transmit data representing the sensed forces and/or acceleration to microprocessor 170 for analysis.

As set forth above, microprocessor 170, if configured for feedback operation, is programmed to actuate the plurality of vibration actuators 150*a* and 150*b* to provide a characteristic vibration based on the forces sensed by force and/or acceleration sensors 130*a*-130*c*, 190 In particular, microprocessor 170 may be operable to provide multiple characteristic vibrations based on the particular forces sensed by force and/or acceleration sensors 130*a*-130*c*, 190. As used herein, the term "characteristic vibration" refers to a specific vibration profile having specific amplitude and frequency characteristics felt by the user's foot due to actuation of vibration actuators 150*a* and 150*b* by microprocessor 170.

Microprocessor 170 may be configured to select the characteristic vibration to be provided based on the forces and/or acceleration sensed by force and/or acceleration sensors 130*a*-130*c*, 190. For example, microprocessor 170 may be programmed to actuate vibration actuators 150*a* and 150*b* to provide a first characteristic vibration when the sensed forces and/or acceleration satisfy a first set of conditions, and a second characteristic vibration different in amplitude, frequency, and/or location of the actuators used when the sensed forces and/or acceleration satisfy a second set of conditions.

Figure 2:
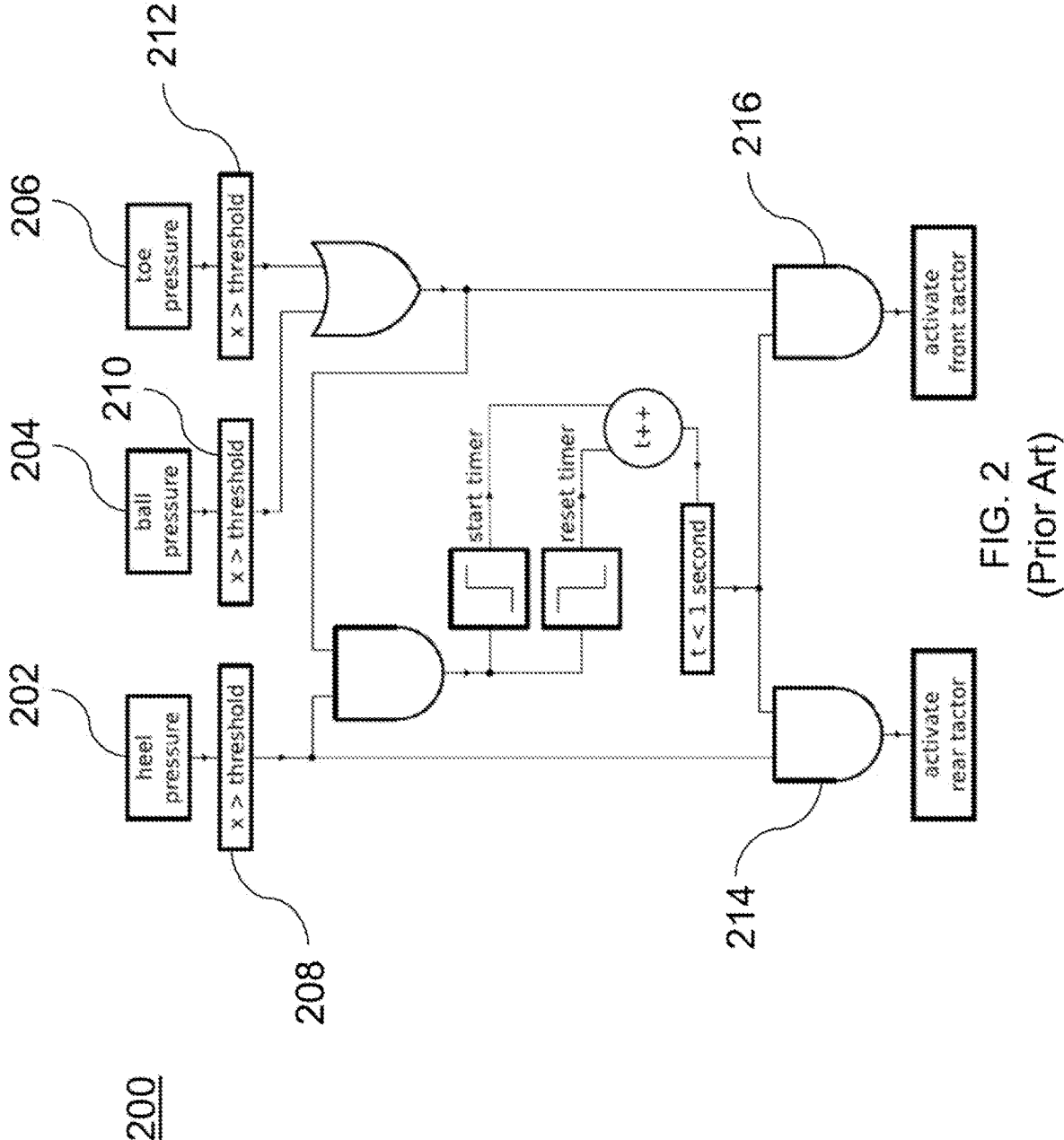
FIG. 2 is a logic diagram illustrating an exemplary operation of the vibratory feedback system of FIG. 1A.

FIG. 2 is a logic diagram 200 illustrating an exemplary operation of vibratory system 100 in Feedback Mode, as described in U.S. Pat. No. 8,692,675. During ambulation by the user, heel sensor 130a senses a force 202 exerted by the user's heel, ball sensor 130b senses a force 204 exerted by the ball of the user's foot, and toe sensor 130c senses a force 206 exerted by the user's toe(s). Each of these forces 202, 204, and 206 has an associated predetermined threshold 208, 210, and 212, such as, for example, a threshold of approximately one pound. As illustrated in FIG. 2, vibration actuators 150a and 150b each have an associated logic gate 214 and 216 for controlling whether the respective actuator is to be actuated.

When (i) force 202 exceeds threshold 208, and (ii) forces 204 and 206 do not exceed thresholds 210 and 212 (i.e. gate 214 is open, and gate 216 is closed), then microprocessor 170 controls rear actuator 150a to provide a first characteristic vibration (i.e. vibrate at a predetermined amplitude and frequency). The frequency may be in the range of approximately 200 Hz to approximately 350 Hz, and more preferably, may be approximately 237 Hz. This first condition may be satisfied by a heel strike during ambulation.

When (i) either force 204 or 206 exceeds its respective threshold 210 or 212, and (ii) force 202 does not exceed threshold 208 (i.e., gate 214 is closed, and gate 216 is opened), then microprocessor 170 controls front actuator 150b to provide a second characteristic vibration. The frequency may be in the range of approximately 200 Hz to approximately 350 Hz, and more preferably, may be approximately 237 Hz. This second condition may be satisfied during the push-off phase of ambulation.

When (i) force 202 exceeds threshold 208, and (ii) either force 204 or 206 exceeds its respective threshold 210 or 212 (i.e. gates 214 and 216 are opened), then microprocessor 170 controls both rear actuator 150a and front actuator 150b to provide a third characteristic vibration. Both vibration actuators 150 may vibrate with a frequency in the range of approximately 3 Hz to approximately 40 Hz, and more preferably, may be approximately 20 Hz. This third condition may be satisfied during the stance phase of ambulation.

It may be desirable to terminate the vibration when the user is no longer walking. Thus, when above-described third condition has been satisfied for a predetermined length of time (e.g., one second), then microprocessor controls vibration actuators 150a and 150b to stop providing the third characteristic vibration (i.e. close gates 214 and 216). Although depicted and described herein with the various phases of gait being determined solely using the force sensors, it should be understood that the acceleration sensor may be used instead of or in addition to the force sensors for determining the phase of gait, and in particular, whether the user is in a stationary stance or ambulating.

Figure 3A:
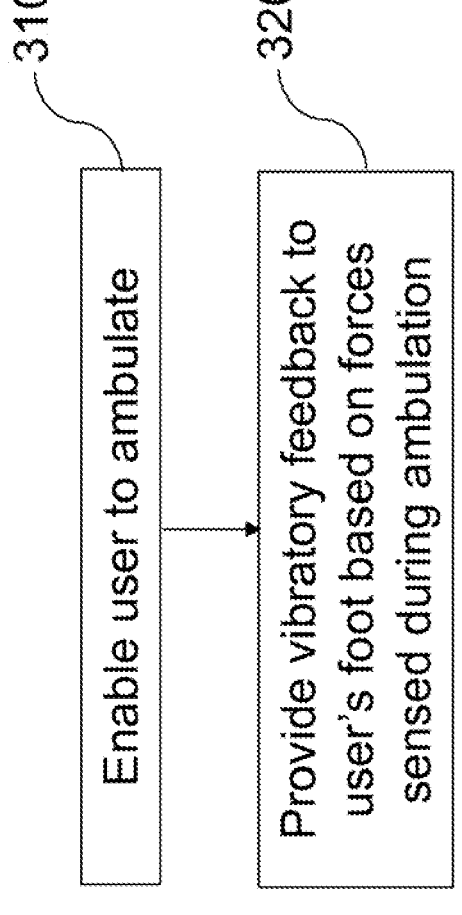
FIG. 3A is a flow chart illustrating an exemplary method for improving the gait of a user in accordance with aspects of the present invention in a Feedback Mode.

FIG. 3A shows an exemplary method for improving the gait of a user 300 in accordance with the Feedback Mode of operation. As a general overview, method 300 includes enabling a user to ambulate and providing a characteristic vibration to the user's foot, based on feedback. Additional details of method 300 are described herein with respect to the components of vibratory system 100 operated in Feedback Mode.

In step 310, a user is enabled to ambulate. In an exemplary embodiment, a user is enabled to ambulate with vibratory system 100 secured to the user's foot. Vibratory system 100 includes a plurality of force sensors 130a-130c configured to sense forces exerted by the user's foot during step 310.

In step 320, a characteristic vibration is provided to the user's foot. In an exemplary embodiment, system 100 provides a characteristic vibration to the user's foot by microprocessor 170 operating vibration actuators 150a and 150b based on the forces sensed by force sensors 130a-130c.

Microprocessor 170 selects the characteristic vibration to be provided based on the forces sensed by force sensors 130a-130c. For example, microprocessor 170 is programmed to actuate vibration actuators 150a and 150b to provide a first characteristic vibration when the sensed forces satisfy a first set of conditions, and a second characteristic vibration different in amplitude and/or frequency when the sensed forces satisfy a second set of conditions. Microprocessor 170 may provide any of the characteristic vibrations (based on any of the conditions) described above with respect to the operation of vibratory feedback system 100.

Method 300 is not limited to the above steps, but may include alternative steps and additional steps, as would be understood by one of ordinary skill in the art from the description herein.

Data Transmittal and Storage

Regardless of mode of operation (Feedback or Continuous), when system 100 includes a data storage component, methods of using the system may comprise the step of storing the data received from force sensors 130a-130c and/or accelerometer 190 in the data storage component, e.g., to facilitate later analysis.

Similarly, when system 100 includes wireless communication device 180, methods of using the system may comprise transmitting the data received from force sensors 130a-130c and/or accelerometer 190 to a remote monitoring unit. In an exemplary embodiment, microprocessor 170 transmits the data received from connected sensors (force sensors, the accelerometer, etc.) to the remote monitoring unit via wireless communication device 180. Microprocessor 170 may further receive data for actuating vibration actuators 150a and 150b from the remote monitoring unit via wireless communication device 180.

In some embodiments, it may be desirable to optimize the characteristic vibration provided by vibratory system 100. Accordingly, method of use may include monitoring the forces sensed by force sensors 130a-130c and/or accelerometer 190 during ambulation by the user (e.g. during step 310), and modifying the characteristic vibration in amplitude or frequency (e.g. as provided during step 320), to create a modified characteristic vibration. These monitoring and modifying steps may be repeated in order to effect a change in the forces exerted by the user (sensed by force sensors 130a-130c) and/or the gait of the user (sensed by accelerometer 190).

In Feedback Mode, when the forces exerted by the user substantially match desired forces, and/or the user's gait substantially matches a desired (or improved) gait, the characteristic vibration may correspond to an optimal characteristic vibration for the user. This optimal characteristic vibration may then be used to provide the vibratory feedback in step 320.

The ability to monitor and control device settings from the remote monitoring unit (e.g. a smartphone wirelessly connected via Bluetooth Low Energy data link to the microprocessor) may permit the wearer to check battery status, monitor and/or control frequency and/or amplitude of vibrations, time span on/off for application of vibration stimulus, and gait parameters. Storage of the vibration and gait data, such as on a secure server "in the cloud" accessible from a communication network (e.g. the Internet) may permit remote monitoring of the information generated by the system by physical therapists, doctors, and/or researchers. The ability to use gait data in this manner may be coupled with machine learning (specific to a particular patient and/or based upon information from a group of wearers of similar systems with medical conditions similar to the wearer) to optimize operation parameters. For example, the vibration characteristics (frequency and/or amplitude) may be optimized for time of day and activity of the wearer.

Continuous Mode

Figure 3B:
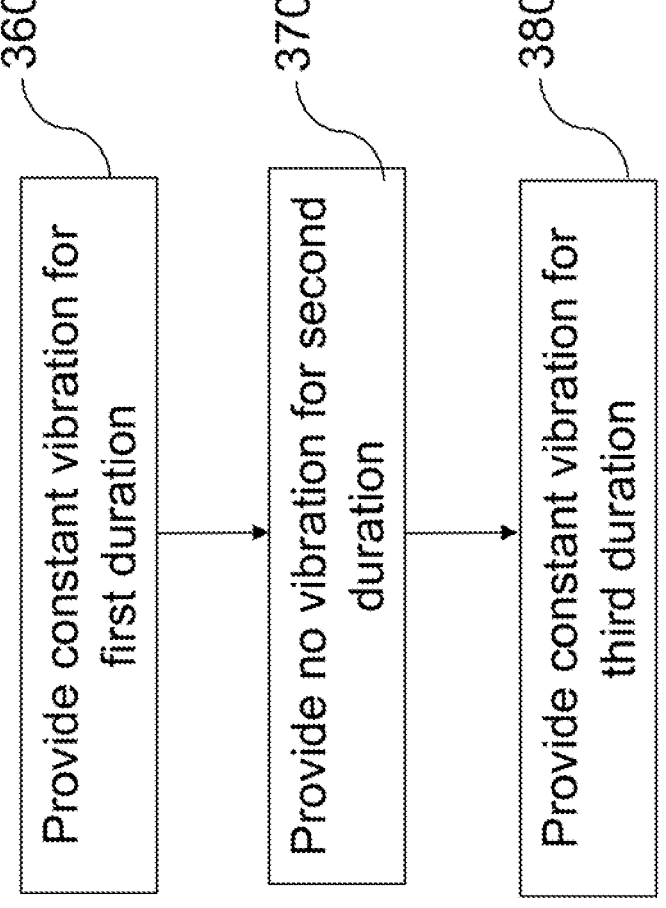
FIG. 3B is a flow chart illustrating an exemplary method for improving the gait of a user in accordance with aspects of the present invention in a Continuous Mode.

In Continuous Mode, a characteristic vibration is applied to the foot of the user by device 100 while the user is walking, turning while walking, standing, or sitting, to improve gait motion. The vibration is not step-synchronized or otherwise directly dependent upon information received from the force sensors or the accelerometer. Accordingly, in continuous-only embodiments, the force sensors and accelerometer are optional, and may not be present. A method 350 of operation in continuous mode, as depicted in FIG. 3B, may be provided intermittently, including steps of providing a first period of continuous vibration 360, providing a second period of no vibration 370, and providing a third period of continuous vibration 380. The on/off durations may be preset, or tailored to a specific patient based upon information provided by the system as to optimal durations for the individual.

While operation in continuous mode may not be directly based upon information generated by the force sensors and/or accelerometer, in embodiments with these elements, such information may be interpreted by the microprocessor as signifying a specific type of activity of the user (e.g. walking straight, turning while walking, standing without walking, or sitting), which information may then be used for selecting a specific mode of vibration from a plurality of continuous mode options. Activity-indicative information may also be used in conjunction with time information, or time information may be used alone, for selecting a specific activity- or time-based mode of vibration. The remote monitor, such as via an application on a mobile device, may also be used for selecting the mode of vibration by the wearer.

Figure 4:
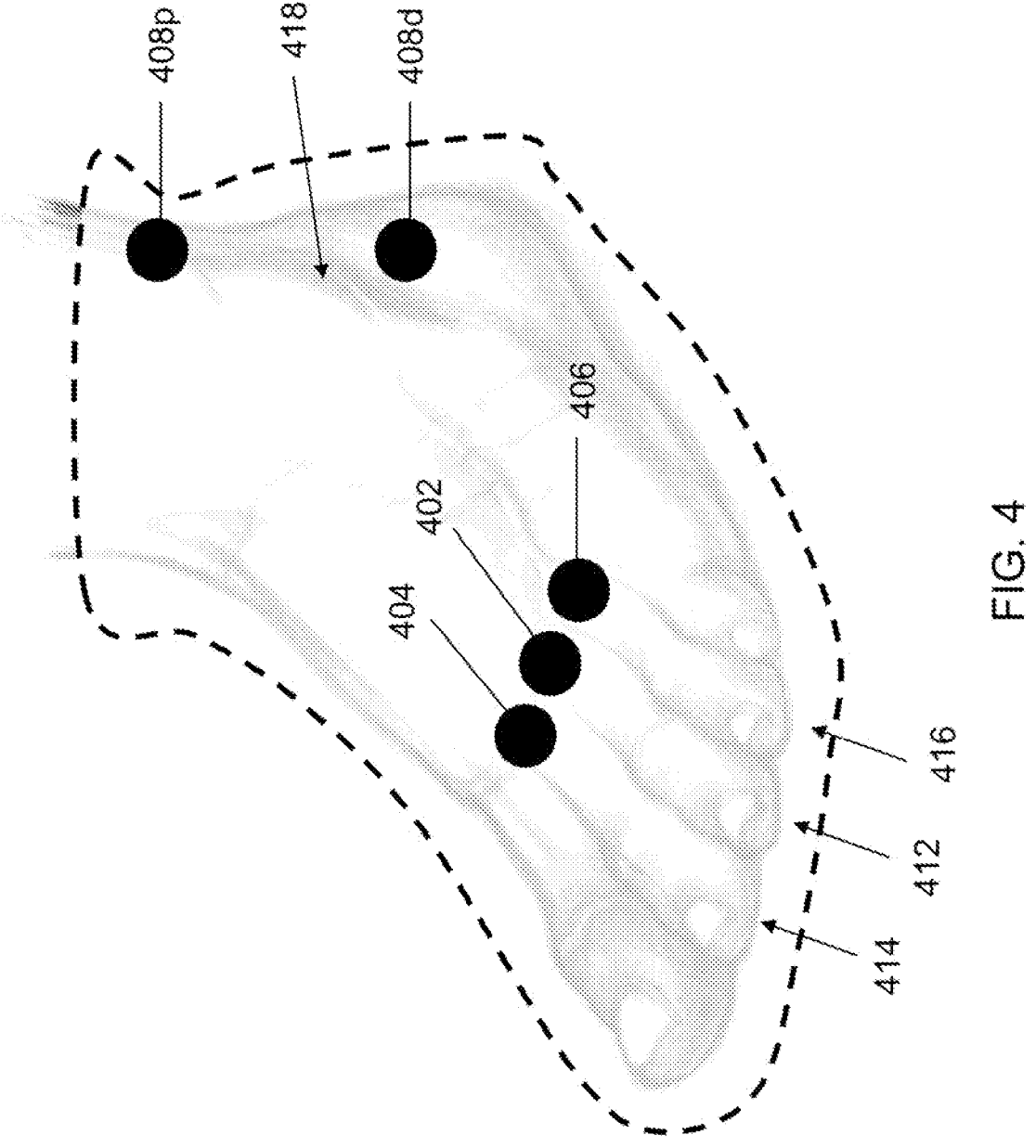
FIG. 4 is a diagram illustrating an exemplary vibration system in accordance with aspects of the present invention.

In preferred embodiments, illustrated in FIG. 4, the plurality of vibration actuators 400 include actuators disposed to provide vibration to a location on a dorsal surface of the wearer's foot, including for example, actuator 402 proximal to at least the 3d toe 412 of the wearer, and optionally also an actuator 404 proximal to the $2^{nd}$ toe (414), an actuator 406 proximal to the $4^{th}$ toe (416), or a combination thereof. The plurality of vibration actuators may also include an actuator disposed to transmit vibration to the inside (i.e. medial aspect) of the ankle, such as an actuator 408p proximal to the malleolus (ankle bone) 418, an actuator 408d distal to the malleolus bone. The plurality of vibration actuators may comprise C-2 tactors provided by Engineering Acoustics, Inc., of Casselberry, FL, or piezoelectric haptic actuators, such as a TDK PiezoHapt™ Actuator such as a model PHUA3015-30A-21-000 actuator from TDK Corporation of Japan, or an EPCOS PowerHap™ such as a model B54103H2020A001 from EPCOS of Munich, Germany (a subsidiary of TDK). The invention is not limited to any particular type, models or manufacturer, however, and the foregoing are provided as examples only.

Without being held to any particular theory, it is believed that vibration stimulation of the peripheral nervous system (i.e. the nervous system outside the brain and spinal cord) stimulates an alternate pathway for movement generation in the basal ganglia (strongly interconnected with the cerebral cortex, thalamus, and brainstem as well as other brain areas) of the brain instead of the usual pathways, which are deficient in PD patients. Such stimulation of neurotransmitters (e.g., biogenic amines) are critical for normal motor function.

EXAMPLES

Three open label, uncontrolled studies support the safety and tolerability of embodiments of the invention. Studies 1 and 2 were previously reported by Winfree et al (2013, 2019). While such open label data are most relevant to safety assessments, these studies (detailed below) also observed improvement in balance and gait, including freezing of gait (FOG) in people with Parkinson's disease.

STEP-SYNCHRONIZED VIBRATION, STUDY 1: The goal of this first study was to preliminarily explore the feasibility, tolerability, safety and impact of external vibration on Parkinson's gait using an early prototype (PDShoe) developed at the University of Delaware. This study included two participants with FOG, one of whom had undergone deep brain stimulation (DBS) surgery. Each participated in 9 sessions of step-synchronized vibration (18 minutes of vibration while walking/session) over the course of 5 days. The synchronized vibration was programmed to activate only when the participant's heel or toes contacted the floor when walking; the vibration turned off when the foot no longer touched the ground or when both feet were in contact with the ground (e.g. standing, sitting).

Results: Both participants with FOG showed improved gait variability, several gait characteristics, and one participant (the one with DBS) reported significant improvement in FOG symptoms.

STEP-SYNCHRONIZED VIBRATION, STUDY 2: Aspects of this study were previously reported in Winfree, K. N., Pretzer-Aboff, I. et al., *Identifying when changes to Parkinsonian gait occur within a vibratory intervention study* [abstract]. Journal of Parkinson's Disease 2013. 3 (suppl. 1). The goal of this study was to investigate the feasibility and impact of step-synchronized vibration in a larger cohort of FOG patients and to assess for any carry-over effect two weeks post-intervention in 17 PD participants with FOG. To enhance the number of participants, the step-synchronized vibration (18 minutes of vibration per session) treatment sessions were simplified to once daily and spread over a period of two weeks. Mean age was 55 (SD 10.1) years, 76% were male, and the mean disease duration 8.9 (SD 5.4) years.

Results: All participants completed the intervention without adverse effects including no incidences of muscle soreness. Fifteen completed the planned follow-up evaluation two weeks post-intervention, and two were lost to follow up due to personal travel plans. Primary data analysis (2 weeks post-intervention, n=15) showed improvements in PD symptoms, coordination, balance, fall efficacy, and quality of life (see Table 1 for details). No significant changes were seen on the Freezing of Gait Questionnaire (FOG-Q) or Timed 10-Meter Walk Test between pre- and follow-up evaluations, although both trended toward improvement.

11

TABLE 1

| Z scores between pretreatment and 2 weeks follow-up treatment | | |
|---|---|---|
| Domain tested | Measure | Z score |
| PD symptoms | Unified Parkinson Disease Rating Scale (UPDRS) part III, motor score | −2.01* |
| Coordination | Timed Up and Go (TUG) | −2.81* |
| Balance | Berg Balance Scale (BBS) | −2.23* |
| Confidence in not falling | Fall Efficacy Scale-International (FES-I) | −2.05* |
| Quality of Life | Parkinson Disease Questionnaire-39 (PDQ-39) | −2.10* |

Note:
*p < 0.05

Secondary analysis of the study 2 data, assessed efficacy of vibration while the vibration was turned on. Vibration effects were analyzed in five randomly selected PD participants from study 2. Each participant performed the following walking protocol: two-minutes without vibration (pre-therapy), three bouts of six-minutes each step-synchronized vibration (therapy), and two minutes again, without vibration (post-therapy). Two-minute rest breaks occurred between each walking bout. Only the first session of the study was considered, as there was no previous exposure to vibration therapy to confound results; five 22-minute sessions were considered in all. Data were sampled at greater than 10 Hz. Turns were removed from the data stream so that all analysis was performed on straight path walking. Each step of the left foot was analyzed for step, stance, and swing duration. Consecutive bouts from each walking session (pre-therapy, therapy, and post-therapy) were merged, with rest periods removed. Change point analysis was performed on each session with 1000 bootstrap re-samplings. The largest change point for step, stance, and swing duration was identified and tested for significance using a confidence level of >90%.

Results: significant changes were observed in all three measures for each participant. These change points were only present in the therapy bouts, indicating an effect of therapy. Change to step duration was not exclusively reflective of a change to either stance or swing duration since both of those also changed. These results support the immediacy of the effect of vibration on PD.

CONTINUOUS VIBRATION, STUDY 3: In Study 2, the investigators noted that several of the participants experienced shuffling of gait; consequently, the shoe vibration was active for much of the intervention. The purpose of Study 3 was to investigate the efficacy of continuous vibration using an advanced, more cost-effective and compact system. Twelve participants with FOG were enrolled: mean age 73.45 (SD 8.5) years, 92% male, and mean PD duration 6.3 (SD 5.0) years.

In this study, continuous vibration was applied to the feet of participants who wore the device while walking for 18 minutes, twice daily for 4 days (Monday, Tuesday, Thursday and Friday) over the course of one week. Wednesday was a rest day (no treatment).

Results: All participants received 100% of the planned treatment sessions and reported comfort of the vibration stimulus without adverse events. Recruitment into the study was completed within two weeks. There were statistically significant improvements in post-treatment scores for mobility (PDQ-39), global spontaneity of movement (UPDRS III), activity of daily living (UPDRS I), and Hoehn & Yahr stage of disease compared to pre-intervention scores. See Table 2 for details. The mean freezing of gait (FOG Q) scores improved (pre=8.92, post=6.92) but were not statistically significant.

TABLE 2

| T-Test between pre and post treatment measurements, N = 12 | | | |
|---|---|---|---|
| Measurement | Pre, M(SD) | Post, M(SD) | t-test |
| UPDRS Part I, activity of daily living | 13.2(7.2) | 9.7(6.4) | 5.2** |
| Hoehn &Yahr stage of disease | 2.7(0.7) | 2.3(0.5) | 2.3* |
| UPDRS, part III-Spontaneity of movement | 1.58(1.2) | 0.67(7.8) | 3.5* |
| PDQ-39 | 45(32.4) | 34(27.8) | 2.9* |

Note:
M = mean, SD = Standard Deviation
*p < 0.05
**p < 0.001

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A vibratory system comprising:
a device adapted to be secured to a lower extremity comprising a foot of a user;
one or more vibration actuators mounted on the device, the one or more vibration actuators configured to provide vibrations to the foot of the user during one or more use cycles, including at least one vibration actuator disposed on the device in a position configured to transmit vibration to a dorsal surface of a $3^{rd}$ toe of the user's foot;
plural sensors comprising a combination of at least one force or pressure sensor, at least one acceleration sensor, and a global positioning system (GPS) sensor, mounted on the device; and
a controller connected to the one or more vibration actuators, the controller programmed to operate the one or more vibration actuators in accordance with a vibration treatment protocol for treating freezing of gait of the user, including:
(a) in a continuous mode in which:
(i) the one or more vibration actuators are activated to provide vibration to the foot of the user according to preset conditions without a dependence upon information sensed by the plural sensors for a first duration,
(ii) then, after (i), no vibration is provided to the foot of the user according to preset conditions without a dependence upon information sensed by the plural sensors for a second duration, and
(iii) then, after (ii), the one or more vibration actuators are activated to provide vibration to the foot of the user according to preset conditions without a dependence upon information sensed by the plural sensors for a third duration; and
(b) in a feedback mode, in which the one or more vibration actuators are activated to provide vibration to the foot of the user based directly upon information sensed by the plural sensors; and
wherein during the one or more use cycles, the controller is further programmed to transition the one or more vibration actuators between providing vibrations to the foot of the user in the continuous mode and providing vibrations to the foot of the user in the feedback mode, wherein the transition is based directly upon information sensed by the GPS sensor.

2. The vibratory system of claim 1, wherein the one or more vibration actuators includes at least one vibration actuator disposed on the device in a position configured to transmit vibration to at least one of a dorsal surface of a $2^{nd}$ toe or a dorsal surface of a $4^{th}$ toe of the user's foot.

3. A method of improving the gait of a user, the method comprising the steps of:

(a) securing a vibratory system to a foot of the user, the vibratory system comprising a device adapted to be secured to a lower extremity comprising a foot of a user, a controller coupled to one or more vibration actuators mounted on the device, the one or more vibration actuators configured to provide vibrations to the foot of the user during one or more use cycles, the controller programmed to operate the one or more vibration actuators in accordance with a vibration treatment protocol for treating freezing of gait of the user, and plural sensors comprising a combination of at least one force or pressure sensor, at least one acceleration sensor, and a global positioning system (GPS) sensor, mounted on the device; and (b) operating the system in a continuous mode comprising the sequential steps of:

(i) providing vibration to the foot of the user by activating the one or more vibration actuators according to preset conditions without a dependence upon information sensed by the plural sensors for a first duration;

(ii) providing no vibration to the foot of the user according to preset conditions without a dependence upon information sensed by the plural sensors for a second duration;

(iii) providing vibration to the foot of the user by activating the one or more vibration actuators according to preset conditions without a dependence upon information sensed by the plural sensors for a third duration; and (c) operating the system in a feedback mode for a fourth duration of time in which the one or more vibration actuators are repeatedly activated and deactivated to provide vibration or no vibration to the foot of the user based directly upon information sensed by the plural sensors; and during the one or more use cycles, providing a transition of the one or more vibration actuators between providing vibrations to the foot of the user in the continuous mode and providing vibrations to the foot of the user in the feedback mode, wherein the transition is based directly upon information sensed by the GPS sensor.

4. The method of claim 3, wherein the plural force or acceleration sensors are configured to sense forces or acceleration exerted by the foot of the user.

5. The method of claim 4, further comprising the steps of:

(d) monitoring the forces sensed by the plural sensors during ambulation by the user; and (e) one or more of:

(i) storing the data received from the plural sensors for analysis, (ii) transmitting the data generated by the plural sensors to a remote monitoring unit.

6. The method of claim 3, wherein the system further comprises a remote monitoring unit in communication with the controller, wherein the method further comprises the step of the controller receiving instructions from the remote monitoring unit for operating the system.

7. The method of claim 3, including providing vibration to a dorsal surface of a $3^{rd}$ toe of the user's foot.

8. The method of claim 7 including providing vibration to at least one of a dorsal surface of a $2^{nd}$ toe or a dorsal surface of a $4^{th}$ toe of the user's foot.

9. The method of claim 3, including providing vibration to a medial aspect of the ankle.

10. The method of claim 3, wherein the method comprises a treatment for Parkinson's disease.

11. The method of claim 10, wherein the method comprises subjecting the user to a vibration treatment protocol comprising multiple cycles of steps (b)(i)-(iii) per day for multiple days.

12. A method of improving the gait of a user, the method comprising the steps of:

(a) securing a vibratory system to a lower extremity comprising a foot of the user, the vibratory system comprising a device comprising a non-cushioned material adapted to be secured to a foot of a user, a sock, a stocking, or a combination thereof, the vibratory system including a controller coupled to one or more vibration actuators mounted on the device and configured to provide vibrations to the foot of the user during one or more use cycles, the controller programmed to operate the one or more vibration actuators in accordance with a vibration treatment protocol for treating freezing of gait of the user, and plural sensors comprising a combination of at least one force or pressure sensor, at least one acceleration sensor, and a global positioning system (GPS) sensor, mounted on the device:

(b) operating the system in a continuous mode comprising the sequential steps of:

(i) providing vibration to the foot of the user for a first duration by activating the one or more vibration actuators according to preset conditions without a dependence upon information sensed by the plural sensors, (ii) providing no vibration to the foot of the user for a second duration according to preset conditions without a dependence upon information sensed by the plural sensors, (iii) providing vibration to the foot of the user for a third duration by activating the one or more vibration actuators according to preset conditions without a dependence upon information sensed by the plural sensors; and (c) operating the system in a feedback mode for a fourth duration of time in which the one or more vibration actuators are repeatedly activated and deactivated to provide vibration or no vibration to the foot of the user based directly upon information sensed by the plural sensors;

during the one or more use cycles, providing a transition of the one or more vibration actuators between providing vibrations to the foot of the user in the continuous mode and providing vibrations to the foot of the user in the feedback mode, wherein the transition is based directly upon information sensed by the GPS sensor;

wherein the method comprises a treatment for Parkinson's disease;

wherein the method comprises subjecting the user to a vibration treatment protocol comprising multiple cycles of steps (b)(i)-(iii) per day for multiple days; and wherein the treatment protocol comprises two consecutive days of treatment, followed by a day of no treatment, followed by two consecutive days of treatment.

13. A vibratory system comprising: a device adapted to be secured to a lower extremity comprising a foot of a user;

one or more vibration actuators mounted on the device, the one or more vibration actuators configured to provide vibrations to the foot of the user during one or more use cycles;

plural sensors comprising at least one force or pressure sensor, at least one acceleration sensor, and a global positioning system (GPS) sensor mounted on the device;

a controller connected to the one or more vibration actuators, the controller programmed to operate the one or more vibration actuators in accordance with a vibration treatment protocol for treating freezing of gait of the user, including:

(a) in a continuous mode in which:

(i) the one or more vibration actuators are activated to provide vibration to the foot of the user according to preset conditions without a dependence upon information sensed by the plural sensors for a first duration, (ii) then, after (i), no vibration is provided to the foot of the user according to preset conditions without a dependence upon information sensed by the plural sensors for a second duration, and (iii) then, after (ii), the one or more vibration actuators are activated to provide vibration to the foot of the user according to preset conditions without a dependence upon information sensed by the plural sensors for a third duration; and (b) in a feedback mode, in which the one or more vibration actuators are activated to provide vibration to the foot of the user based directly upon information sensed by the plural sensors; and wherein during the one or more use cycles, the controller is further programmed to transition the one or more vibration actuators between providing vibrations to the foot of the user in the continuous mode and providing vibrations to the foot of the user in the feedback mode, wherein the transition is based directly upon information sensed by the GPS sensor.

14. The vibratory system of claim 13, wherein the force or acceleration sensor is configured to sense forces or acceleration exerted by the foot of the user.

15. The vibratory system of claim 14, wherein the controller is connected to a data storage component configured to store data generated by the plural sensors.

16. The vibratory system of claim 14, further comprising:

a wireless communication device in communication with the controller and with a remote monitoring unit, wherein the controller is programmed to transmit the data received from the plurality of force or acceleration sensors to the remote monitoring unit via the wireless communication device.

17. The vibratory system of claim 16, wherein the controller is programmed to receive instructions for operating the system from the remote monitoring unit via the wireless communication device.

18. The vibratory system of claim 14, wherein the controller is programmed to process information sensed by the plural sensors to determine an activity of the user, and to impose a continuous mode of vibration selected based upon the activity so determined.

19. The vibratory system of claim 13, wherein the one or more vibration actuators includes at least one vibration actuator disposed on the device in a position configured to transmit vibration to a medial aspect of the ankle.

* * * * *